United States Patent [19]

Stollar et al.

[11] Patent Number: 4,849,547
[45] Date of Patent: Jul. 18, 1989

[54] METHOD FOR THE PREPARATION OF DECABROMODIPHENYL ETHER

[75] Inventors: Hyman Stollar; Khaim Khariton; Mark Grinberg; Eva Ellmann, all of Beer-Sheva, Israel

[73] Assignee: Bromine Compounds Limited, Israel

[21] Appl. No.: 108,095

[22] Filed: Oct. 13, 1987

[30] Foreign Application Priority Data

Oct. 22, 1986 [IL] Israel .................................... 80390

[51] Int. Cl.$^4$ .............................................. C07C 41/20
[52] U.S. Cl. .................................................. 568/639
[58] Field of Search ................................ 568/635, 639

[56] References Cited

U.S. PATENT DOCUMENTS 4,521,633  6/1985  Pedjac ................................... 568/639

FOREIGN PATENT DOCUMENTS

| 2236362 | 2/1974 | Fed. Rep. of Germany | 568/639 |
| 0039639 | 3/1977 | Japan | 568/639 |
| 0222043 | 12/1983 | Japan | 568/639 |
| 1472383 | 5/1977 | United Kingdom | 568/639 |
| 2143521 | 2/1985 | United Kingdom | 568/639 |

Primary Examiner—Werren B. Lone
Attorney, Agent, or Firm—Lerner, David, Littenberg, Krumholz & Mentlik

[57] ABSTRACT

A process for the preparation of decabromodiphenyl ether by the reaction of diphenyl ether or of a partially brominated derivative thereof, in a mixture of halogenated organic solvents is described.

The process of the invention provides a product having improved thermal stability. The process can be carried out in a quasi-steady state manner, thereby producing a product with constant quality.

11 Claims, No Drawings

METHOD FOR THE PREPARATION OF DECABROMODIPHENYL ETHER

BACKGROUND OF THE INVENTION (a) The Field of the Invention

The present invention relates to a process for the preparation of Decabromodiphenyl ether. More particularly, the present invention relates to a process which employs a mixture of halogenated organic solvents, by which Decabromodiphenyl ether is obtained, having improved thermal stability.

Decabromodiphenyl ether, hereinafter referred to as "DECA" for the sake of brevity, is a well known flame retardant agent, useful in the preparation of articles made of polymeric material, to which it is desired to impart flame-retardant properties.

(b) The Prior Art

According to the known art DECA is prepared in a variety of solvents, ranging from liquid bromine to halogenated organic solvents. U.S. Pat. No. 4,521,633 discloses one of such processes in which DECA is prepared by reacting diphenyl ether in methylene chloride (dichloromethane) with a brominating agent in the presence of a catalyst, by initiating the reaction at a temperature of 15° C. or lower, and then raising the temperature of the reaction mixture to an elevated temperature.

U.S. Pat. No. 3,959,387 discloses a process for the preparation of polybrominated biphenyl oxides in which the reaction is carried out in methylene bromide as the solvent, at temperatures of from room temperature to 200° C.

The above and other processes according to the art employ substantially pure halogenated solvents, such as substantially pure methylene chloride or methylene bromide. When organic solvents are employed for the preparation of DECA, it is a generally accepted principle in the art that the solvent must be a substantially pure solvent. Thus, for instance, U.S. Pat. No. 4,521,633 states that the use of methylene chloride is particularly advantageous in that it exhibits very low susceptibility to transhalogenation. Similarly, U.S. Pat. No. 3,959,387 teaches that the use of methylene bromide as the solvent is necessary to the conduction of the reaction.

The use of pure chlorine-containing solvents, according to the art, has the considerable drawback of requiring costly and time-taking purification steps, because of the transhalogenation that takes place during the reaction with solvents such as methylene chloride. Reaction of diphenyl oxide with a brominating agent in methylene chloride in the presence of a bromination catalyst inevitably causes some transhalogenation of the solvent to take place, which results in the presence of measurable amounts of both bromochloromethane and dibromomethane in the reaction mixture. These transhalogenation products must be separated before the methylene chloride is reused in a subsequent run.

SUMMARY OF THE INVENTION

It has now been surprisingly found, and this is an object of the present invention, that it is possible to prepare DECA in a mixture of halogenated organic solvents, and to obtain a product with high yield and good quality.

It has further been found, and this is another object of the invention, that it is possible to operate in a quasi-steady state manner, when producing DECA in several subsequent batches according to the process of the invention.

It has also been found, and this is still another object of the present invention, that, in order to obtain a product having good thermal stability, the process of the invention must be carried out at a maximal reaction temperature that does not exceed a predetermined limit.

DETAILED DESCRIPTION OF THE INVENTION

The process for the preparation of decabromodiphenyl ether according to the invention is characterized in that diphenyl ether, or one or more partially brominated diphenyl ether derivative(s), is brominated in a mixture of solvents comprising at least two of the solvents dichloromethane, bromochloromethane and dibromomethane in the presence of a bromination catalyst, the maximal reaction temperature not exceeding 80° C.

A preferred embodiment of the invention is characterized by the steps of:

(a) preparing a solution of a brominating agent and a bromination catalyst in a mixture of solvents comprising at least two of the solvents dichloromethane, bromochloromethane and dibromomethane;

(b) providing liquid diphenyl ether or a partially brominated diphenyl ether derivative, or a mixture of two or more such derivatives, in molten form, or in a solvent selected from among dichloromethane, bromochloromethane and dibromomethane, or a mixture of two or more of said solvents;

(c) adding the said liquid diphenyl ether or brominated diphenyl ether derivative(s) to solution (a), thereby initiating the reaction;

(d) continuing the reaction at a temperature equal to or lower than 80° C.;

(e) recovering the product from the reaction mixture;

(f) recovering the mixture of organic solvents from the reaction mixture; and (g) recycling the mixture of organic solvents to the reaction vessel, optionally adding a solvent selected from among dichloromethane, bromochloromethane and dibromomethane or a mixture thereof as a makeup.

It is of course possible to employ a solid starting material rather than a liquid material. This, while permissible, is impractical, as it will be apparent to the man of the art. According to a preferred embodiment of the invention, the partially brominated diphenyl ether derivative is selected from Pentabromodiphenyl ether (PENTA) and Octabromodiphenyl ether (OCTA). It should be noted that such partially brominated derivatives comprise a mixture of differently brominated diphenyl ethers. Thus PENTA, for instance, characterizes a product having an average content of five bromine atoms per molecule. Likewise, OCTA is not a single compound but a mixture of brominated derivatives having an average content of eight bromine atoms per diphenyl ether moecule.

Preferably, step (c) is carried out at a temperature lower than 25° C., more preferably about −5° C. to 5° C.

According to a preferred embodiment of the invention the brominating agent is bromine. According to another preferred embodiment of the invention, the bromination catalyst is an aluminum catalyst, selected from among metallic aluminum, $AlCl_3$ and $AlBr_3$.

According to a still preferred embodiment of the invention the makeup consists essentially of methylene chloride.

According to a still more preferred embodiment of the invention the process is carried out in a quasi-steady state manner, as herein defined. According to this preferred embodiment, the total amount of make-up solvent mixture added to the recycled solvent mixture and the proportions between dichloromethane, bromochloromethane and dibromomethane in the said make-up are such that addition of the make-up to the recycled solvent mixture will provide a solvent mixture having a content of dichloromethane, bromochloromethane and dibromomethane substantially equal to that of the previous batch. If diphenyl ether is added in solution, rather than in its pure melted form, then the solvent employed for preparing this solution will be considered as a part of the makeup, for the above purposes.

As it will be readily appreciated by a person skilled in the art, the invention provides a very economical and convenient process. After a batch has been prepared, the organic layer is separated from the aqueous layer, which is formed from water added during the separation steps, and the resulting solvent mixture is distilled without fractionation. $H_2O$ is removed by azeotropic distillation or by addition of a drying agent before distillation. Of course, some organic solvent may be lost during these operations, and a makeup may be required. Such a makeup can consist of any of the solvents present in the mixture, or of a mixture thereof in any proportion, if available from another source. Moreover, the makeup can be added so to obtain a solvent mixture which is desirable for a certain reaction, e.g. a solvent mixture having a specified reflux temperature, lower than 80° C.

Ideally, it is possible to start from any given solvent mixture and to recycle and reuse it until nearly all the solvent has been converted to dibromomethane. For practical purposes, however, it is preferred to operate with mixtures that do not contain too high fractions of dibromomethane and, therefore, the makeup solvent will usually contain amounts of dibromomethane as low as possible. Usually, it will be preferred to use dichloromethane as the makeup solvent, for cost reasons.

According to the process of the invention it is possible to operate in a quasi-steady state manner, when producing DECA in the solvent mixture of the invention. This is achieved by adding to the solvent mixture recovered from the previous batch an amount of solvent, having any determined desired proportions in the mixture, so that when the make-up solvent has been added the resulting solvent mixture will have substantially the same proportions between the three different solvents that were present at the beginning of the previous batch, from which the body of the solvent was recovered. Obviously, this presents the considerable advantage of affording a process that operates substantially at the same conditions in each separate batch, and therefore gives the same results as any other batch of DECA produced in this semi-steady state process.

As it will be apparent to a person skilled in the art, this process solves many problems related to quality and operating parameters, since substantially identical reaction conditions can be achieved each time. In practice, when operating in a quasi-steady state, as herein defined, there is no need to carry out any treatment of the solvent mixture, other than the inevitable removal of water, since when the same amount of the same make-up solvent is added in each new batch to the solvent recovered from the previous batch, the solvent mixture so obtained will be substantially the same that was employed in the previous batch, having the same composition and behaviour as in any one of the previous batches prepared during the quasi-steady state production.

Furthermore, it is possible, whenever required, to effect a bleeding of the recycled solvent mixture, in order to reduce the level of any impurities which might accumulate in the solvent mixture. The make-up added will then be able to replace also the solvent removed through bleeding, and not only any solvent lost during operations in the previous batch. In any case, quasi-steady state conditions can be obtained, with or without bleeding, as it will be apparent to the man of the art. Usually, when the solvent from a completed batch is evaporated and transferred to the next batch, some solvent is left on purpose in the reaction vessel to simplify removal of solid impurities that are soluble therein and which would otherwise deposit on the reactor walls and be more difficult to remove. Therefore an operation comparable to what is normally termed "bleeding" is usually effected, although it is likewise possible to evaporate all the solvent and to remove the solid from the reactor by any other means.

The thermal stability of a flame retardant agent such as DECA is a very important requirement. In order to be usefully employed as additives to various plastics, flame retardant agents must be colorless, since coloration of the flame retardant additive results in the change in color of the article which incorporates it. Thermal instability of the FR agent results in its change from colorless to colored when heated, for example, during the incorporation process. This change in color may derive from the inherent thermal instability of the FR agent or from the presence of impurities in the product, which impart a thermal instability to it. It is therefore clear that thermal stability is of paramount importance for obtaining articles with acceptable color after the incorporation process. DECA itself is thermally stable and derives its thermal instability from impurities formed during its preparation, the exact nature of which is unknown. The applicant has now surprisingly found that thermal stability of the DECA produced according to the process of the invention is obtained, if the reaction temperature does not exceed 80° C. When operating with the process of the invention, using mixtures containing less than about 50% (v/v) dibromomethane, the reflux temperature is lower than 75° C. Therefore, when operating with such mixtures the condition for obtaining thermally stable DECA is always met, and the process can be carried out without any special precautions regarding the reaction temperature.

The above and other characteristics and advantages of the invention will be better understood through the following illustrative and non-limitative examples.

EXAMPLE 1

To a one-liter flask equipped with a mechanical stirrer, a dropping funnel, a thermometer and a reflux condenser there were added 430 ml of a mixture containing 26% v/v dichloromethane, 8% v/v bromochloromethane and 66% v/v dibromomethane, 7.5 g of anhydrous $AlCl_3$ and 880 g of bromine (5.5 moles). The contents of the flask were cooled to about 0° C. and a solution of 85 g (0.5 mole) of diphenyl ether in 20 ml dichloromethane was added dropwise to the stirred mixture during 2 hours, while maintaining the temperature between 0° and 5° C. After completion of the addition, the contents of the flask were heated between 64° and 75° C. during 5 hours. After this time, the reaction was stopped by adding 60 ml of water, and unreacted bromine was bleached by adding a concentrated aqueous sodium bisulfite solution. The aqueous layer was separated and the organic phase was washed twice with 150 ml portions of water and was then neutralized with an aqueous sodium hydroxide solution. The mixture was filtered and the white product was washed with water and dried in a vacuum oven at about 70° C. HPLC analysis gave a 96% content of DECA in the product (m.p. 302—304).

Thermal stability was checked by heating the product in an oven for 2 hours at 280° C. Color deviation was checked by visual observation with reference to the unheated product. After heating was completed no appreciable change of color was observed.

The organic layer from the filtrate was distilled and was found to contain 4% dichloromethane, 33% bromochloromethane and 63% dibromomethane. This mixture was reused in the subsequent run, after addition of 125 ml dichloromethane as the makeup.

EXAMPLE 2 (COMPARATIVE)

Example 1 was repeated, with the exception that 100% dibromomethane was used and when the addition of the diphenyl ether was completed the contents of the flask were heated at temperatures between 80° C. and reflux (about 92° C.) for 2-5 hours, until completion of the reaction. The product was analysed by HPLC and was found to contain 96% DECA (m.p. 302°-304° C.). The resulting product was heated at 280° C. for 2 hours, after which period it became colored.

EXAMPLES 3 THROUGH 8

Example 1 was repeated in different solvent mixtures. The results and main conditions for each run are summarized in Table I below.

TABLE I

| Example | Solvent % (v/v) | | | AlCl$_3$ (gr)* | Max. Temp. (°C.)(+) | React. time (hrs) | % DECA (HPLC) |
|---|---|---|---|---|---|---|---|
| | MC | CBM | DBM | | | | |
| 3 | 10 | 0 | 90 | 7.5 | 75 | 5.5 | 94.5 |
| 4 | 16 | 20 | 64 | 7.5 | 75 | 5.3 | 96.1 |
| 5 | 26 | 8 | 66 | 7.5 | 75 | 4.5 | 94.8 |
| 6 | 31 | 23 | 46 | 10 | 70 | 4.5 | 97.9 |
| 7 | 45 | 45 | 10 | 10 | 60 | 6.0 | 95.1 |
| 8 | 70 | 25 | 5 | 10 | 51 | 7.3 | 96.1 |

MC - dichloromethane
CBM - bromochloromethane
DBM - dibromomethane
*AlCl$_3$ anhydrous
(+)Maximal reaction temperature

EXAMPLE 9

Quasi-Steady State Operation 190 ml of a solvent mixture containing 62% v/v dichloromethane, 29% v/v bromochloromethane and 9% v/v dibromomethane was mixed with 180 ml dichloromethane. Bromination of diphenyl ether was carried out following the procedure of Example 1, with 0.5 moles diphenyl ether, 5.5 moles bromine, 15 g AlCl$_3$, a maximal reaction temperature of 52° C. and a reaction time (post addition) of 7.5 hours. The reaction was repeated several times, by recycling the solvent mixture as hereinbefore described. The mean reaction yield was 96%.

Table II below shows the composition of the solvent mixture at different stages of the process, for three consecutive runs. It should be noted that in this laboratory experiment no special care was taken to avoid solvent losses. In industrial operation, however, solvent losses can be very much reduced by taking appropriate care during operation, as apparent to the man of the art.

TABLE II

| | Volume (ml)[1] | | Before Reaction Content (%)[2] | | | After Reaction Content (%)[3] | | | Recycle Content (%)[4] | | |
|---|---|---|---|---|---|---|---|---|---|---|---|
| Run | solv. | make-up | MC | CBM | DBM | MC | CBM | DBM | MC | CBM | DBM |
| 1 | 215 | 155 | 60 | 22 | 6 | 36 | 51 | 13 | 32 | 53 | 15 |
| 2 | 190 | 180 | 62 | 29 | 9 | 39 | 51 | 10 | 35 | 53 | 12 |
| 3 | 190 | 180 | 67 | 27 | 6 | 36 | 50 | 14 | 45 | 43 | 11 |

MC -dichloromethane
CBM -bromochloromethane
DBM -dibromomethane
[1]Volume of recycled solvent and of make-up
[2]Solvents mixture composition before the reaction
[3]Solvents mixture composition after the reaction
[4]Solvents mixture composition after the reaction and after evaporation (recycled mixture).

As it can be seen from the data in the above table, addition of the appropriate amount of make-up results in a semi-steady state operation. The process may be continued indefinitely, by adding the same amount of make-up, and the solvent mixture composition will vary within relatively narrow limits from one batch to the other. Furthermore, the make-up can be finely controlled, if desired, by means known to a person skilled in the art, to obtain a narrow limit for the desired steady state.

The above examples have been provided for the purpose of illustration, and are not intended to be limitative. Many variations can be effected in the various means and procedures. For instance, different proportions can be employed in the solvent mixture, or lower maximal reaction temperatures can be used, all without exceeding the scope of the invention.

What we claim is:

1. A process for the preparation of decabromodiphenyl ether comprising brominating one or more aromatic compounds selected from the group consisting of diphenyl ether and the partially brominated derivatives thereof in a reaction mixture including bromine, a bromination catalyst selected from the group consisting of metallic aluminum, AlCl$_3$ and AlBr$_3$ and a predetermined ratio of two or more organic solvents selected from the group consisting of dichloromethane, bromochloromethane and dibromomethane.

2. The process of claim 1, which further includes recovering said organic solvents from said reaction mixture and recycling said recovered organic solvents for the further preparation of decabromodiphenyl ether.

3. The process of claim 1, including maintaining said reaction mixture at a temperature lower than about 80° C.

4. The process of claim 1 including providing said reaction mixture and adding said aromatic compounds to said reaction mixture.

5. The process of claim 4, including providing said reaction mixture at a first temperature lower than about 25° C., and heating said reaction mixture to a second temperature lower than about 80° C. following the addition of said aromatic compounds.

6. The process of claim 5, wherein said first temperature is between about −5° C. and 5° C.

7. The process of claim 1, wherein said predetermined ratio of said two or more organic solvents comprises less than about 50% dibromomethane by volume.

8. The process of claim 7 including providing said reaction mixture at the reflux temperature of said predetermined ratio of said organic solvent.

9. The process of claim 2, which further includes adding a predetermined quantity and ratio of one or more organic solvents selected the group consisting of dichloromethane, bromochloromethane and dibromomethane to said recovered organic solvents for recycling therewith.

10. The process of claim 9, wherein said predetermined quantity and ratio of said one or more organic solvents are selected so as to provide an organic solvent mixture having substantially the same organic solvent ratio as said predetermined ratio of said two or more organic solvents.

11. The process of claim 9, wherein said one or more organic solvents primarily comprises dichloromethane.

* * * * *